United States Patent [19]

Corbett

[11] Patent Number: 4,722,689
[45] Date of Patent: Feb. 2, 1988

[54] COATED TEMPORARY DENTAL CROWNS

[76] Inventor: Jack A. Corbett, 902 Whitestone, Houston, Tex. 77073

[21] Appl. No.: 811,103

[22] Filed: Dec. 20, 1985

[51] Int. Cl.[4] .............................................. A61C 13/22
[52] U.S. Cl. ..................................... 433/218; 433/219; 433/23; 433/17
[58] Field of Search ..................... 433/218, 219, 23, 17

[56] References Cited

U.S. PATENT DOCUMENTS

| 3,504,438 | 4/1970 | Wittman et al. | 433/23 X |
| 4,050,156 | 9/1977 | Chasanoff et al. | 433/218 X |
| 4,120,090 | 10/1978 | Kesling | 433/23 |
| 4,363,624 | 12/1982 | Johnston | 433/219 X |
| 4,498,867 | 2/1985 | Kesling | 433/17 X |

Primary Examiner—Nancy A. B. Swisher
Attorney, Agent, or Firm—Margaret A. Boulware

[57] ABSTRACT

A coated metallic dental crown and orthodontic appliances which are coated with a thin layer tooth-colored polymer which resembles the normal tooth. The appearance of temporary dental crowns and orthodontic appliances is metallic and the coated crowns and appliance blend with the teeth to give a more pleasing appearance in the mouth.

5 Claims, 3 Drawing Figures

COATED TEMPORARY DENTAL CROWNS

BACKGROUND OF THE INVENTION

This invention is directed to dental crowns and dental and orthodontic appliances and enhancing their appearance for the patient by applying a polymeric, tooth-colored coating. Permanent crowns are often a tooth-colored dental ceramic which is tinted to blend with the rest of the teeth of a patient. When the patient has dental procedures in progress, an exposed portion of the tooth which is very sensitive has to be covered by a temporary crown. These crowns are made of malleable metal shells, which resemble the tooth to be replaced. The dentist has available temporary crowns which match the typical shape of various size of molars, bicuspids and other teeth which are in the process of dental restoration. Also available are aluminum temporary caps which are cylindrical without anatomy on a flat occlusal surface.

The temporary crown is worn during the time that a permanent crown is being made. The temporary crown is metallic usually of an aluminum, stainless steel, tin/silver alloy, other alloys or anodized metal. It is necessary to have a malleable material so that the temporary crown can be cut and trimmed to provide a comfortable bite on the occlusal surface of the opposite tooth. Also, the crown must be crimped around the base of the remaining portion of the tooth to provide a smooth, comfortable and secure fit.

The metal temporary crown used have an unattractive appearance. There are metallic crowns with a gold colored anodized layer, but this is not a tooth-colored layer which blends in appearance with the patient's teeth. This type of crown was disclosed in U.S. Pat. No. 3,422,535 in which the anodized layer to a metal crown provided an insulated coating to prevent discomfort due to galvanic action between the crown and other metals used for dental work such as silver fillings and gold restoration. The crown would have a metallic appearance with the gold-colored dye.

Another area of interest for natural looking appliances is the orthodontic and dental field. More and more adults as well as young people are turning to orthodontic correction. The appliances used in the mouth have been made of metallic materials that include bands which slip around the teeth, cleats which are glued on the front of the teeth and stainless steel wires which connect the various appliances to arrange the teeth in proper alignment. The metallic appliances are quite unattractive and recent improvements included use of clear polymer appliances with the stainless steel wires. Certain parts of dental appliances will benefit with a natural look. The wires used to hold partial plates can be coated to blend in with the patient's teeth.

SUMMARY OF THE INVENTION

This invention is for dental crowns and dental and orthodontic appliances which are coated with a tooth-colored polymer composition. The coating is a very thin layer that will adhere to the crown or appliance during manipulation necessary for applying the crown or appliance in the mouth. The coating adheres to the malleable metal parts and does not peel or chip under normal use and mastication when the crown is cut and applied properly. The coating can be made of nylon, epoxy, polyesters, vinyls, rubber, silicone rubber or acrylics which will carry the pigment to give the natural tooth color. The coating material also must have a curing temperature in a range that will not affect the integrity of the metal crown or orthodontic appliance.

The coated crowns and orthodontic appliances of this invention are functional and do not detract from the patient's appearance as do the metal or partially metal devices. The pigment included in the coating is matched to correlate to the color of a tooth and thereby blend in with the teeth in the patient's mouth. The coating is durable and pliable so that it does not peel or rub off during use. The coating also functions as an insulating layer so that a galvanic potential does not occur in the mouth with other metals used for dental care.

The invention will be described in further detail with reference to the examples shown in the drawings in which.

Figure 1:
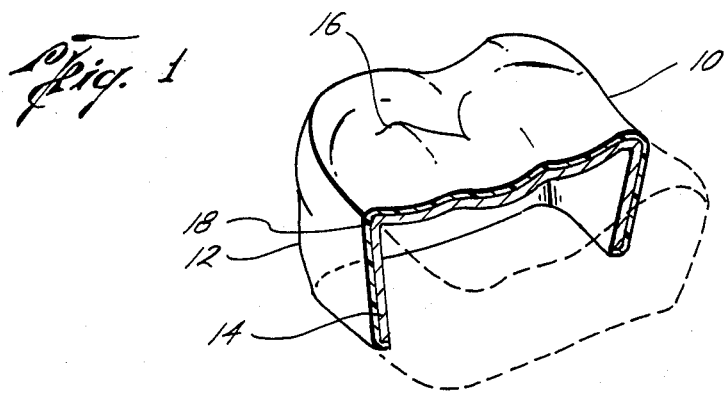
FIG. 1 is a cross-section of a dental crown.

Referring to FIG. 1 is a cross-section of a dental crown 10 which is shaped to resemble the tooth which it replaces. The temporary crown is sized to fit comfortably over the portion of the tooth on which the dental procedure is being performed. The side portion 12 is trimmed so that the bottom edge of the crown meets the gum line in a comfortable manner approximating the placement of the tooth when the crown is applied. The crowns are manufactured in size and shapes to fit the various types of teeth. The crown is made of a malleable metallic layer 14 which can be crimped around the base of the tooth and shaped on the occlusal surface 16 to provide a comfortable bite with the opposing tooth. It is important that the base be trimmed to provide the proper height for the crown to give a good fit. The metallic layer is any malleable metal including aluminum, stainless steel, tin/silver alloy, other alloys and anodized metals.

The metal layer is covered by tooth-colored coating 18 which is preferably 5 mils or less in thickness. The polymer layer can be any type of coating which will carry tooth-colored pigment and cure at a temperature at which the integrity of the metal layer 14 remains intact. The coating must have enough pliability so that it will crimp with the metal layer around the tooth portion to be protected and mold on the occlusal surface when the crown is conformed to provide a comfortable bite with the opposing tooth. The coating 18 must adhere to the metallic layer 14 so that it does not peel or chip off during normal wear by the patient. Suitable coating materials are nylon, epoxy, polyesters, vinyls, rubber, silicone rubber and acrylics.

Aluminum, tin/silver alloy, aluminum anodized and stainless steel crowns have been coated with a nylon 11 resin. The tooth-colored pigment was achieved by using a mixture of titanium dioxide and yellow iron oxide. The nylon 11 resin was applied by deposition of fine powder which has been charged on the grounded temporary crown work piece. Prior to coating the crown is prepared to remove any soil by vapor degreasing, alkaline cleaning or ultra-sonic cleaning as needed. Any surface oxides may be removed and surface activation can be accomplished by acid treatment or abrasive blasting according to the metal or alloy work piece. It has been found that when using nylon 11 a primer coat of an epoxy phenolic system is used to give better coating adhesion. A preferred epoxy phenolic system is Corvel® NC-P-200 a proprietary compound of the polymer corporation of Reading, Pa. The Corvel® NC-P-200 is applied in a layer of about 0.1 to about 0.2 mils thick.

The nylon 11 resin is compounded to a fine powder with the pigments titanium dioxide and yellow iron oxide, and an epoxy resin curing agent. The titanium dioxide and yellow iron oxide pigments can be used in varying amounts depending on the shade of tooth enamel desired to be reproduced. It has been found that about 3 percent titanium dioxide and about 0.075 percent yellow iron oxide per weight of nylon 11 resin gives a natural tooth enamel appearance.

A substantial part of the powder can pass through a 425 mesh and is a sprayable product. The aerated powder in a semi-fluid state passes by an electrode which imparts a charge on the powder. The charged powder is directed toward metallic crown which has been prepared as described above and coats the crown with a fine layer of powder.

The powder coated crown is placed in a curing oven so that the nylon and curing agent forms a film. When using aluminum and tin/silver base material for the crowns the temperature is kept around 400° F. and cured for 10–15 minutes. Stainless steel crowns will withstand curing temperatures for most polymer systems. The nylon coating is about 3–5 mils thick after curing.

An epoxy layer can be coated on a crown prepared in the same manner as described above. When using an epoxy resin, a primer coat is not necessary. Also, some epoxies cure with a yellow coloration so titanium dioxide is added as a white pigment to adjust the color of the final product to resemble the tooth color. The resins of choice are epoxy phenolic compounded with titanium dioxide. A fine powder is prepared and applied to the work piece as described above. An epoxy system that will cure at 300°–400° F. is used for aluminum and tin/silver crowns. Resin systems have a range of curing temperatures that can be selected according to the temperature the metal can withstand. The epoxy coating generally is 2–3 mils thick.

An example of an epoxy coating system that has been found satisfactory includes the following components.

TABLE I

| Epoxy Resin GT 7014 | Ciba Geigy | 62.3% |
| Phenolic Hardener XU 251 | Ciba Geigy | 27.7% |
| Resiflow PF | GCA Chemical Corp. | 1.0% |
| Titanium Dioxide R-900 | DuPont | 10.0% |

The sample epoxy coating system in Table I is exemplary and other systems with similar coating and color properties can be used to practice the invention.

Figure 2:
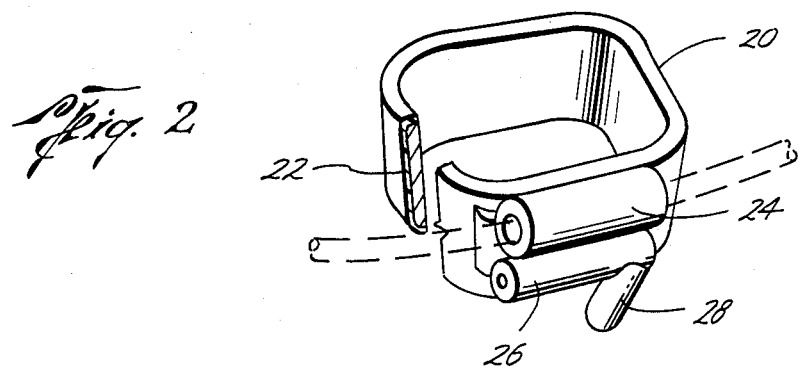
FIG. 2 is an orthodontic band in partial cross-section and perspective view.

In addition to the temporary dental crowns that are coated, orthodontic appliances and wires have been similarly coated. FIG. 2 shows an enlarged view of an orthodontic band 20 which can be coated in a manner as described for the dental crowns. The band 20 encircles a tooth and tubular member 24 holds a wire which is threaded through the band and used to apply the pressure on the tooth for the necessary alignment correction. The smaller member 26 with knob 28 extending therefrom is also used for wrapping the wire. The band 20 is shown in partial cross-section to show coating layer 22 which covers the appliance. The fine powder used for deposition can be directed into the smaller crevices and around the small tubular members to apply an even coating.

Figure 3:
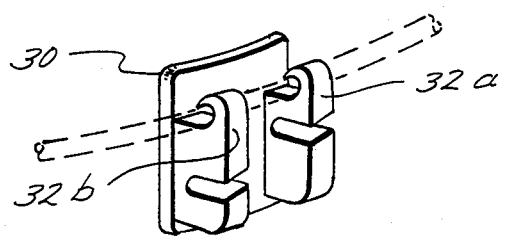
FIG. 3 is a perspective view of a cleat.

FIG. 3 is an enlarged view of a cleat 30 which is glued to the patients front teeth. The cleats have brackets 32a and 32b which channel the wires used for alignment. The cleat shown in FIG. 3 is coated with the tooth colored resin. The metallic cleats and bands are quite unattractive particularly when the patient wears these appliances on the front teeth. Also, stainless wires have been coated successfully. Since all the metal parts can be coated with a tooth-colored resin, the braces are far less noticeable and much more attractive than the metal orthodontic appliances.

What is claimed is:

1. A dental appliance comprising a temporary dental crown for covering and protecting a portion of a human tooth which has been the subject of a dental procedure, a malleable metallic shell sized to cover the tooth portion and provide a comfortable bite to the opposing tooth and the outer surface of the crown covered with tooth-colored polymer wherein said polymer coating is selected from the group consisting of nylon, polyester vinyls, epoxy, rubber, silicone rubber and acrylic which cures at a temperature compatible with maintaining the integrity of the metallic shell.

2. A dental appliance of claim 1 wherein said malleable metallic shell for the temporary crown is selected from the group consisting of stainless steel, aluminum, tin/silver alloy and anodized metals.

3. A dental appliance of claim 1 wherein the pigment to provide the tooth-color is selected from the group of titanium dioxide, yellow iron oxide, and mixtures thereof.

4. A dental appliance comprising
   a temporary dental crown for covering and protecting a portion of a human tooth which has been the subject of a dental procedure, a shell selected from aluminum, tin/silver alloy, anodized aluminum or stainless steel sized to cover the remaining portion of the tooth and provide a corresponding bite to the opposing tooth and the outer surface of said temporary crown coated with Nylon 11 about 2 mils thick which has effective amounts of titanium dioxide and yellow iron oxide to give a tooth-colored coating which coating has been applied over a primer coat of about 0.1 to about 0.2 mils epoxy phenolic system CORVEL ®.

5. A dental appliance comprising a temporary crown for covering and protecting a portion of a human tooth which has been the subject of a dental procedure, a shell selected from the group consisting of aluminum, tin/silver, anodized aluminum or stainless steel sized to cover the remaining portion of the tooth and provide a corresponding bite to the opposing tooth and the outer surface of said temporary crown coated with a phenolic cured epoxy with an effective amount of titanium dioxide pigment.

* * * * *